US006656720B2

(12) United States Patent
Gröner et al.

(10) Patent No.: US 6,656,720 B2
(45) Date of Patent: *Dec. 2, 2003

(54) ANIMAL CELLS AND PROCESSES FOR THE REPLICATION OF INFLUENZA VIRUSES

(75) Inventors: Albrecht Gröner, Seeheim (DE); Jürgen Vorlop, Marburg (DE)

(73) Assignee: Chiron Behring GmbH & Co., Marburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/194,784

(22) Filed: Jul. 12, 2002

(65) Prior Publication Data

US 2003/0073223 A1 Apr. 17, 2003

Related U.S. Application Data

(63) Continuation of application No. 09/155,581, filed as application No. PCT/IB97/00403 on Apr. 1, 1997, now Pat. No. 6,455,298.

(30) Foreign Application Priority Data

Apr. 1, 1996 (DE) .......................................... 196 12 966

(51) Int. Cl.$^7$ .............................. C12N 7/00; C12N 7/02; C12N 5/06
(52) U.S. Cl. ...................... 435/235.1; 435/239; 435/350
(58) Field of Search .............................. 435/235.1, 239, 435/350

(56) References Cited

U.S. PATENT DOCUMENTS

| | | | |
|---|---|---|---|
| 4,064,232 A | 12/1977 | Bachmayer et al. | |
| 4,500,513 A | 2/1985 | Brown et al. | ............... 435/236 |
| 4,783,411 A | 11/1988 | Gabliks | ...................... 435/237 |
| 5,753,489 A * | 5/1998 | Kistner et al. | ........... 435/235.1 |
| 6,455,298 B1 * | 9/2002 | Groner et al. | ........... 435/235.1 |

FOREIGN PATENT DOCUMENTS

| | | |
|---|---|---|
| EP | 00/19218 | 11/1980 |
| EP | 0 389 925 | 12/1995 |
| GB | 1070764 | 6/1965 |
| WO | WO 91/09937 | 7/1991 |
| WO | WO 96/15231 | 5/1996 |
| WO | WO 96/15232 | 5/1996 |
| WO | WO 97/11093 | 3/1997 |
| WO | WO 97/37000 | 10/1997 |
| WO | WO 97/37001 | 10/1997 |

OTHER PUBLICATIONS

Merten et al. Advances in Experimental Medicine and Biology 297:141–151,1996.*
Hougland et al. Growth 42(2): 1790188, 1978 (Abstract only cited).*
Rodriguez–Boulan et al. Journal of Cell Biology 96:866–874, 1983.*
Alonso–Caplen et al. Journal of Cell Biology 97: 659–668, 1983.*
Skibbens et al. Journal of Cell Biology 108:821–832, 1989.*
Mancini et al. Revista de Farmacia e Bioquimica da Universidade de Sao Paulo, 1993, 29*2(, 89–95.*
Brumback, B.G. et al. "Rapid culture for influenza virus, types A and B, in 96–well plates", *Clinical and Diagnostic Virology*, 1995, 4, 251–256.
Frank, A.L. et al., "Comparision of different tissue cultures for isolation and quantitation of influenza and parainfluenza viruses", *Jrl. of Clinical Microbiology*, 1979, 10(1), 32–36.
Mancini, et al., "Evalation of the "in vitro" multiplication of influenza virus and the enzymatic influence on viral growth", *Revista de Farmacia e Bioquimica da Universidade de Sao Paulo*, 1993, 29(2), 89–95, English abstract provided.
Orlich M. et al., "Structural variation occurring in the hemagglutinin of influenza virus A/Turkey/Oregon/71 during adaptation to different cell types", *Virology*, 1990, 176, 531–538.
Pridgen, C.L., "Influenza virus RNAs in the cytoplasm of chicken embryo cells treated with 3'–deoxyadenosine", *Jrl. of Virology*, 1976, 18(1), 356–360.
Leland, D.S. & Harmon, M.W., Lennette, E.H. ed., *Laboratory Diagnosis of Viral Infections*, $2^{nd}$ Edition, 1992, pp 19–20 and 526–527.
Tannock, et al., "Evaluation of chicken kidney and chicken embryo kidney cultures for the large–scale growth of attenuated influenza virus master strain", *Vaccine*, 1985, 3(3), 333–9, Database Dialog # 05806807.
Kilbourne, E.D., *Influenza*, 1987, Plenum Medical Book, 89–110.
Klenk, et al., "Activation of Influenza A Viruses by Trypsin Treatment", *Virology*, 1975, 68, 426–439.
Lazarowitz, et al., "Enhancement of the Infectivity of Influenza A and B Viruses by Proteolytic Cleavage of the Hemmagglutinin Polypeptide", *Virology*, 1975, 68, 440–454.
Merten, et al., "Production of Influenza Virus in Cell Cultures for Vaccine Preparation", *Advances in Experimental Medicine and Biology*, 1996, 397, 141–151.
Tobita, et al., "Plaque Assay and Primary Isolation of Influenza A Viruses in an Established Line of Canine Kidney Cells (MDCK) in the Presence of Trypsin", *Med. Microbiol. Immunol.*, 1975, 162, 9–14.

(List continued on next page.)

*Primary Examiner*—Mary E. Mosher
(74) *Attorney, Agent, or Firm*—Rebecca M. Hale; Dale Hoscheit; Robert P. Blackburn

(57) ABSTRACT

Animal cells are described which can be infected by influenza viruses and which are adapted to growth in suspension in serum-free medium. Processes for the replication of influenza viruses in cell culture using these cells are furthermore described, as well as vaccines which contain the influenza viruses obtainable by the process or constituents thereof

43 Claims, No Drawings

OTHER PUBLICATIONS

Perrin, et al., "An Experimental Rabies Vaccine Produced with a New BHK–21 Suspension Cell Culture Process: Use of Serum Free Medium and Perfusion –Reactor System", *Vaccine*, 1995, 13(13), 1244–1250.

Yamaoka et al, Arch Virol (1995) 140: 937–944.

Fields et al, Eds., Fields Virology, Second Edition, Raven Press, New York, New York (1990) 1:1092–1093.

Brown et al, Eds., Inactivated Influenza Vaccines Prepared in Cell Culture, Developments in Biological Standardization, S. Karger AG, Basel, Switzerland (1999) 98:13–21.

Jennings et al, Vaccine, (1984) 2:75–80.

Govorkova et al, JID (1995) 172:250–3.

Bulletin of the World Heath Organization (1995) 73:431–435.

Robertson et al, Vaccine (1995) 13:1583–1588.

Derwent Biotechnology Abstracts Accession No. 84–06431, HEESE (1984) Patent No. DE 3237313 (English Language Abstract) (full German text patent attached).

Govorkova et al, J. Virol (1996) 70(8):5519–5524.

Bachmayer, Intervirology, (1975) 5:260–272.

Palache et al, JID (1997) 176 (Suppl. 1): S20–23.

Brands et al, Proceedings of the third International Conference on Options for the Control of Influenza, Options for the Control of Influenza III, Brown et al, Editors. Elsevier Science B.V., Amsterdam (1996), 683–693.

* cited by examiner

ANIMAL CELLS AND PROCESSES FOR THE REPLICATION OF INFLUENZA VIRUSES

This application is a continuation of application Ser. No. 09/155,581, filed Sep. 29, 1998, now U.S. Pat. No. 6,455, 298 which is a National Phase application of International Application serial no. PCT/IB97/00403, filed Apr. 1, 1997, which claims priority to German application serial no. 196 12 966.4, filed Apr. 1, 1996. The disclosure of each of the foregoing is hereby incorporated by reference in its entirety.

The present invention relates to animal cells which can be infected by influenza viruses and are adapted to growth in suspension in serum-free medium, and to processes for the replication of influenza viruses in cell culture using these cells. The present invention further relates to the influenza viruses obtainable by the process described and to vaccines which contain viruses of this type or constituents thereof.

All influenza vaccines which have been used since the 40s until today as permitted vaccines for the treatment of humans and animals consist of one or more virus strains which have been replicated in embryonate hens' eggs. These viruses are isolated from the allantoic fluid of infected hens' eggs and their antigens are used as vaccine either as intact virus particles or as virus particles disintegrated by detergents and/or solvents—so-called cleaved vaccine—or as isolated, defined virus proteins—so-called subunit vaccine. In all permitted vaccines, the viruses are inactivated by processes known to the person skilled in the art. The replication of live attenuated viruses, which are tested in experimental vaccines, is also carried out in embryonate hens' eggs.

The use of embryonate hens' eggs for vaccine production is time-, labor- and cost-intensive. The eggs—from healthy flocks of hens monitored by veterinarians—have to be incubated before infection, customarily for 12 days. Before infection, the eggs have to be selected with respect to living embryos, as only these eggs are suitable for virus replication. After infection the eggs are again incubated, customarily for 2 to 3 days. The embryos still alive at this time are killed by cold and the allantoic fluid is then obtained from the individual eggs by aspiration. By means of laborious purification processes, substances from the hen's egg which lead to undesired side effects of the vaccine are separated from the viruses, and the viruses are concentrated. As eggs are not sterile (pathogen-free), it is additionally necessary to remove and/or to inactivate pyrogens and all pathogens which are possibly present.

Viruses of other vaccines such as, for example, rabies viruses, mumps, measles, rubella, polio viruses and FSME viruses can be replicated in cell cultures. As cell cultures originating from tested cell banks are pathogen-free and, in contrast to hens' eggs, are a defined virus replication system which (theoretically) is available in almost unlimited amounts, they make possible economical virus replication under certain circumstances even in the case of influenza viruses. Economical vaccine production is possibly also achieved in that virus isolation and purification from a defined, sterile cell culture medium appears simpler than from the strongly protein-containing allantoic fluid. The isolation and replication of influenza viruses in eggs leads to a selection of certain phenotypes, of which the majority differ from the clinical isolate. In contrast to this is the isolation and replication of the viruses in cell culture, in which no passage-dependent selection occurs (Oxford, J. S. et al., J. Gen. Virology 72(1991),185–189; Robertson, J. S. et al., J. Gen. Virology 74 (1993) 2047–2051). For an effective vaccine, therefore, virus replication in cell culture is also to be preferred from this aspect to that in eggs.

It is known that influenza viruses can be replicated in cell cultures. Beside hens' embryo cells and hamster cells (BHK21-F and HKCC), MDBK cells, and in particular MDCK cells have been described as suitable cells for the in-vitro replication of influenza viruses (Kilbourne, E. D., in: Influenza, pages 89–110, Plenum Medical Book Company-New York and London, 1987). A prerequisite for a successful infection is the addition of proteases to the infection medium, preferably trypsin or similar serine proteases, as these proteases extracellularly cleave the precursor protein of hemagglutinin [$HA_0$] into active hemagglutinin [$HA_1$ and $HA_2$]. Only cleaved hemagglutinin leads to the adsorption of the influenza viruses on cells with subsequent virus assimilation into the cells (Tobita, K. et al., Med. Microbiol. Immunol., 162 (1975),9–14; Lazarowitz, S. G. & Choppin, P. W., Virology, 68 (1975) 440–454; Klenk, H.-D. et al., Virology 68 (1975) 426–439) and thus to a further replication cycle of the virus in the cell culture.

The Patent U.S. Pat. No. 4,500,513 described the replication of influenza viruses in cell cultures of adherently growing cells. After cell proliferation, the nutrient medium is removed and fresh nutrient medium is added to the cells with infection of the cells with influenza viruses taking place simultaneously or shortly thereafter. A given time after the infection, protease (e.g. trypsin) is added in order to obtain an optimum virus replication. The viruses are harvested, purified and processed to give inactivated or attenuated vaccine. Economical influenza virus replication as a prerequisite for vaccine production cannot be accomplished, however, using the methodology described in the patent mentioned, as the change of media, the subsequent infection as well as the addition of trypsin which is carried out later necessitates opening the individual cell culture vessels several times and is thus very labor-intensive. Furthermore, the danger increases of contamination of the cell culture by undesirable micro-organisms and viruses with each manipulation of the culture vessels. A more cost-effective alternative is cell proliferation in fermenter systems known to the person skilled in the art, the cells growing adherently on microcarriers. The serum necessary for the growth of the cells on the microcarriers (customarily fetal calf serum), however, contains trypsin inhibitors, so that even in this production method a change of medium to serum-free medium is necessary in order to achieve the cleavage of the influenza hemagglutinin by trypsin and thus an adequately high virus replication. Thus this methodology also requires opening of the culture vessels several times and thus brings with it the increased danger of contamination.

The present invention is thus based on the object of making available cells and processes which make possible simple and economical influenza virus replication in cell culture. This object is achieved by the provision of the embodiments indicated in the patent claims. The invention thus relates to animal cells which can be infected by influenza viruses and which are adapted to growth in suspension in serum-free medium. It was found that it is possible with the aid of cells of this type to replicate influenza viruses in cell culture in a simple and economical manner. By the use of the cells according to the invention, on the one hand a change of medium before infection to remove serum can be dispensed with an on the other hand the addition of protease can be carried out simultaneously to the infection. On the whole, only a single opening of the culture vessel for infection with influenza viruses is thus necessary, whereby the danger of the contamination of the cell cultures is drastically reduced. The expenditure of effort which would be associated with the change of medium, the infection and the subsequent protease addition is furthermore decreased. A further advantage is that the consumption of media is markedly decreased.

The cells according to the invention are preferably vertebrate cells, e.g. avian cells, in particular hens' embryo cells. In a particularly preferred embodiment, the cells according to the invention are mammalian cells, e.g. from hamsters, cattle, monkeys or dogs, in particular kidney cells or cell lines derived from these. They are preferably cells which are derived from MDCK cells (ATCC CCL34 MDCK (NBL-2)), and particularly preferably cells of the cell line MDCK 33016. This cell line was deposited under the deposit number DSM ACC2219 on Jun. 7, 1995 according to the requirements of the Budapest Convention for the International Recognition of the Deposition of Micro-organisms for the Purposes of Patenting in the German Collection of Micro-organisms (DSM), in Brunswick, Federal Republic of Germany, recognized as the international deposition site. The cell line MDCK 33016 is derived from the cell line MDCK by passaging and selection with respect to the capability of growing in suspension in serum-free medium and of replicating various viruses, e.g. orthomyxoviruses, paramyxoviruses, rhabdoviruses and flavoviruses. On account of these properties, these cells are suitable for economical replication of influenza viruses in cell culture by means of a simple and cost-effective process.

The present invention therefore also relates to a process for the replication of influenza viruses in cell culture, in which cells according to the invention are used, in particular a process which comprises the following steps:

i) proliferation of the cells according to the invention described above in serum-free medium in suspension;
ii) infection of the cells with influenza viruses;
iii) addition of protease shortly before, simultaneously to or shortly after infection; and
iv) further culturing of the infected cells and isolation of the replicated influenza viruses.

The cells according to the invention can be cultured in the course of the process in various serum-free media known to the person skilled in the art (e.g. Iscove's medium, ultra CHO medium (BioWhittaker), EX-CELL (JRH Biosciences)). Otherwise, the cells for replication can also be cultured in the customary serum-containing media (e.g. MEM or DMEM medium with 0.5% to 10%, preferably 1.5% to 5%, of fetal calf serum) or protein-free media (e.g. PF-CHO (JRH Biosciences)). Suitable culture vessels which can be employed in the course of the process according to the invention are all vessels known to the person skilled in the art, such as, for example, spinner bottles, roller bottles or fermenters.

The temperature for the proliferation of the cells before infection with influenza viruses is preferably 37° C. Culturing for proliferation of the cells (step (i)) is carried out in a preferred embodiment of the process in a perfusion system, e.g. in a stirred vessel fermenter, using cell retention systems known to the person skilled in the art, such as, for example, centrifugation, filtration, spin filters and the like.

The cells are in this case preferably proliferated for 2 to 18 days, particularly preferably for 3 to 11 days. Exchange of the medium is carried out in the course of this, increasing from 0 to approximately 1 to 3 fermenter volumes per day. The cells are proliferated up to very high cell densities in this manner, preferably up to approximately $2 \times 10^7$ cells/ml. The perfusion rates during culture in the perfusion system can be regulated both via the cell count, the content of glucose, glutamine or lactate in the medium and via other parameters known to the person skilled in the art. For infection with influenza viruses, about 85% to 99%, preferably 93 to 97%, of the fermenter volume is transferred with cells to a further fermenter. The cells remaining in the first fermenter can in turn be mixed with medium and replicated further in the perfusion system. In this manner, continuous cell culture for virus replication is available.

Alternatively to the perfusion system, the cells in step (i) of the process according to the invention can preferably also be cultured in a batch process. The cells according to the invention proliferate here at 37° C. with a generation time of 20 to 30 h up to a cell density of about 8 to $25 \times 10^5$ cells/ml.

In a preferred embodiment of the process according to the invention, the pH of the culture medium used in step (i) is regulated during culturing and is in the range from pH 6.6 to pH 7.8, preferably in the range from pH 6.8 to pH 7.3.

Furthermore, the $pO_2$ value is advantageously regulated in this step of the process and is preferably between 25% and 95%, in particular between 35% and 60% (based on the air saturation). According to the invention, the infection of the cells cultured in suspension is preferably carried out when the cells in the batch process have achieved a cell density of about 8 to $25 \times 10^5$ cells/ml or about 5 to $20 \times 10^6$ cells/ml in the perfusion system.

In a further preferred embodiment, the infection of the cells with influenza viruses is carried out at an m.o.i. (multiplicity of infection) of about 0.0001 to 10, preferably of 0.002 to 0.5. The addition of the protease which brings about the cleavage of the precursor protein of hemagglutinin [$HA_0$] and thus the adsorption of the viruses on the cells, can be carried out according to the invention shortly before, simultaneously to or shortly after the infection of the cells with influenza viruses. If the addition is carried out simultaneously to the infection, the protease can either be added directly to the cell culture to be infected or, for example, as a concentrate together with the virus inoculate. The protease is preferably a serine protease, and particularly preferably trypsin.

In a preferred embodiment, trypsin is added to the cell culture to be infected up to a final concentration of 1 to 200 μg/ml, preferably 5 to 50 μg/ml, and particularly preferably 5 to 30 μg/ml in the culture medium. During the further culturing of the infected cells according to step (iv) of the process according to the invention, trypsin reactivation can be carried out by fresh addition of trypsin in the case of the batch process or in the case of the perfusion system by continuous addition of a trypsin solution or by intermittent addition. In the latter case, the trypsin concentration is preferably in the range from 1 μg/ml to 80 μg/ml.

After infection, the infected cell culture is cultured further to replicate the viruses, in particular until a maximum cytopathic effect or a maximum amount of virus antigen can be detected. Preferably, the culturing of the cells is carried out for 2 to 10 days, in particular for 3 to 7 days. The culturing can in turn preferably be carried out in the perfusion system or in the batch process.

In a further preferred embodiment, the cells are cultured at a temperature of 30° C. to 36° C., preferably of 32° C. to 34° C., after infection with influenza viruses. The culturing of the infected cells at temperatures below 37° C., in particular in the temperature ranges indicated above, leads to the production of influenza viruses which after inactivation have an appreciably higher activity as vaccine, in comparison with influenza viruses which have been replicated at 37° C. in cell culture.

The culturing of the cells after infection with influenza viruses (step (iv)) is in turn preferably carried out at regulated pH and $pO_2$. The pH in this case is preferably in the range from 6.6 to 7.8, particularly preferably from 6.8 to 7.2, and the $pO_2$ in the range from 25% to 150%, preferably from 30% to 75%, and particularly preferably in the range from 35% to 60% (based on the air saturation).

During the culturing of the cells or virus replication according to step (iv) of the process, a substitution of the cell culture medium with freshly prepared medium, medium concentrate or with defined constituents such as amino acids, vitamins, lipid fractions, phosphates etc. for optimizing the antigen yield is also possible.

After infection with influenza viruses, the cells can either be slowly diluted by further addition of medium or medium concentrate over several days or can be incubated during further perfusion with medium or medium concentrate decreasing from approximately 1 to 3 to 0 fermenter volumes/day. The perfusion rates can in this case in turn be regulated by means of the cell count, the content of glucose, glutamine, lactate or lactate dehydrogenase in the medium or other parameters known to the person skilled in the art.

A combination of the perfusion system with a fed-batch process is further possible. In a preferred embodiment of the process, the harvesting and isolation of the replicated influenza viruses is carried out 2 to 10 days, preferably 3 to 7 days, after infection. To do this, for example, the cells or cell residues are separated from the culture medium by means of methods known to the person skilled in the art, for example by separators or filters. Following this the concentration of the influenza viruses present in the culture medium is carried out by methods known to the person skilled in the art, such as, for example, gradient centrifugation, filtration, precipitation and the like.

The invention further relates to influenza viruses which are obtainable by a process according to the invention. These can be formulated by known methods to give a vaccine for administration to humans or animals. The immunogenicity or efficacy of the influenza viruses obtained as vaccine can be determined by methods known to the person skilled in the art, e.g. by means of the protection imparted in the loading experiment or as antibody titers of neutralizing antibodies. The determination of the amount of virus or antigen produced can be carried out, for example, by the determination of the amount of hemagglutinin according to methods known to the person skilled in the art. It is known, for example, that cleaved hemagglutinin binds to erythrocytes of various species, e.g. to hens' erythrocytes. This makes possible a simple and rapid quantification of the viruses produced or of the antigen formed.

Thus the invention also relates to vaccines which contain influenza viruses obtainable from the process according to the invention. Vaccines of this type can optionally contain the additives customary for vaccines, in particular substances which increase the immune response, i.e. so-called adjuvants, e.g. hydroxide of various metals, constituents of bacterial cell walls, oils or saponins, and moreover customary pharmaceutically tolerable excipients.

The viruses can be present in the vaccines as intact virus particles, in particular as live attenuated viruses. For this purpose, virus concentrates are adjusted to the desired titer and either lyophilized or stabilized in liquid form.

In a further embodiment, the vaccines according to the invention can contain disintegrated, i.e. inactivated, or intact, but inactivated viruses. For this purpose, the infectiousness of the viruses is destroyed by means of chemical and/or physical methods (e.g. by detergents or formaldehyde). The vaccine is then adjusted to the desired amount of antigen and after possible admixture of adjuvants or after possible vaccine formulation, dispensed, for example, as liposomes, microspheres or "slow release" formulations.

In a further preferred embodiment, the vaccines according to the invention can finally be present as subunit vaccine, i.e. they can contain defined, isolated virus constituents, preferably isolated proteins of the influenza virus. These constituents can be isolated from the influenza viruses by methods known to the person skilled in the art.

Furthermore, the influenza viruses obtained by the process according to the invention can be used for diagnostic purposes. Thus the present invention also relates to diagnostic compositions which contain influenza viruses according to the invention or constituents of such viruses, if appropriate in combination with additives customary in this field and suitable detection agents. The examples illustrate the invention.

EXAMPLE 1

Preparation of Cell Lines Which are Adapted to Growth in Suspension and can be Infected by Influenza Viruses A cell line which is adapted to growth in suspension culture and can be infected by influenza viruses is selected starting from MDCK cells (ATCC CCL34 MDCK (NBL-2), which had been proliferated by means of only a few passages or over several months in the laboratory. This selection was carried out by proliferation of the cells in roller bottles which were rotated at 16 rpm (instead of about 3 rpm as is customary for roller bottles having adherently growing cells). After several passages of the cells present suspended in the medium, cell strains growing in suspension were obtained. These cell strains were infected with influenza viruses and the strains were selected which produced the highest virus yield. An increase in the rate of cells growing in suspension during the first passages at 16 rpm is achieved over 1 to 3 passages by the addition of selection systems known to the person skilled in the art, such as hypoxanthine, aminopterin and thymidine, or alanosine and adenine, individually or in combination. The selection of cells growing in suspension is also possible in other agitated cell culture systems known to the person skilled in the art, such as stirred flasks.

Alternatively, highly virus-replicating cell clones can be established before selection as suspension cells by cell cloning in microtiter plates. In this process, the adherently growing starting cells (after trypsinization) are diluted to a concentration of about 25 cells/ml with serum-containing medium and 100 µl each of this cell suspension are added to a well of a microtiter plate. If 100 µl of sterile-filtered medium from a 2 to 4-day old (homologous) cell culture ("conditioned medium") are added to each well, the probability of growth of the cells inoculated at a very low cell density increases. By means of light-microscopic checking, the wells are selected in which only one cell is contained; the cell lawn resulting therefrom is then passaged in larger cell culture vessels. The addition of selection media (e.g. hypoxanthine, aminopterin and thymidine, or alanosine and adenine, individually or in combination) after the 1st cell passage leads over 1 to 3 passages to a greater distinguishability of the cell clones. The cell clones resulting in this way were selected with respect to their specific virus replication and then selected as suspension cells. The selection of cells which are adapted to growth in serum-free medium can also be carried out by methods known to the person skilled in the art.

Examples of cells which are adapted to growth in serum-free medium in suspension and can be infected by influenza viruses are the cell lines MDCK 33016 DSM ACC2219) and MDCK 13016, whose properties are described in the following examples.

EXAMPLE 2
Replication of Influenza Viruses in the Cell Line MDCK 33016

The cell line MDCK 33016 (DSM ACC2219; obtained from an MDCK cell culture by selection pressure) was proliferated at 37° C. in Iscove's medium with a splitting rate of 1:8 to 1:12 twice weekly in a roller bottle which rotated at 16 rpm. Four days after transfer, a cell count of approximately $7.0 \times 10^5$ to $10 \times 10^5$ cells/ml was achieved. Simultaneously to the infection of the now 4-day old cell culture with the influenza virus strain A/PR/8/34 (m.o.i.= 0.1), the cell culture was treated with trypsin (25 µg/ml final concentration) and cultured further at 37° C., and the virus replication was determined over 3 days (Table I).

TABLE I

Replication of influenza A/PR/8/34 in roller bottles (cell line MDCK 33016) after infection of a cell culture without change of medium, measured as antigen content (HA units)

| | HA content after days after infection (dpi) | | |
|---|---|---|---|
| | 1 dpi | 2 dpi | 3 dpi |
| Experiment 1 | 1:64 | 1:512 | 1:1024 |
| Experiment 2 | 1:4 | 1:128 | 1:1024 |
| Experiment 3 | 1:8 | 1:32 | 1:512 |

The ratios indicated mean that a 1:X dilution of the virus harvest still has hemagglutinating properties. The hemagglutinating properties can be determined, for example, as described in Mayer et al., Virologische Arbeitsmethoden, [Virological Working Methods], Volume 1 (1974), pages 260–261 or in Grist, Diagnostic Methods in Clinical Virology, pages 72 to 75.

EXAMPLE 3
Replication of Influenza Viruses in the Cell Line MDCK 13016 in Spinner Bottles The cell line MDCK 13016 was replicated at 37° C. in Iscove's medium with a splitting rate of 1:6 to 1:10 twice weekly in a spinner bottle (50 rpm). Four days after transfer, a cell count of $8.0 \times 10^5$ cells/ml was achieved. Simultaneously to the infection of the now 4-day old cell culture with the influenza virus strain A/PR/8/34 (m.o.i.=0.1), the cell culture was treated with trypsin (25 µg/ml final concentration) and incubated further at 33° C. and the virus replication was determined over 6 days (Table II).

TABLE II

Replication of influenza A/PR/8/34 in spinner bottles (cell line MDCK 13016) after infection of a cell culture without change of medium, measured as antigen content (HA units)

| | HA content after days after infection (dpi) | | | | |
|---|---|---|---|---|---|
| | 1 dpi | 3 dpi | 4 dpi | 5 dpi | 6 dpi |
| Experiment 1 | 1:2 | 1:128 | 1:1024 | 1:1024 | 1:2048 |
| Experiment 2 | 1:4 | 1:512 | 1:2048 | 1:2048 | 1:1024 |

EXAMPLE 4
Replication of Various Influenza Strains in the Cell Line MDCK 33016 in Roller Bottles The cell line MDCK 33016 (DSM ACC2219) was replicated at 37° C. in Iscove's medium with a splitting rate of 1:8 to 1:12 twice weekly in a roller bottle which rotated at 16 rpm. Four days after transfer, a cell count of approximately $7.0 \times 10^5$ to $10 \times 10^5$ cells/ml was achieved. Simultaneously to the infection of the now 4-day old cell culture with various influenza virus strains (m.o.i. 0.1), the cell culture was treated with trypsin (25 µg/ml final concentration) and further incubated at 33° C., and the virus replication was determined on the 5th day after infection (Table III).

TABLE III

Replication of influenza strains in roller bottles (cell line MDCK 33016) after infection of a cell culture without change of medium, measured as antigen content (HA units)

| | HA content 5 days after infection |
|---|---|
| Influenza strain | HA content |
| A/Singapore/6/86 | 1:1024 |
| A/Sichuan/2/87 | 1:256 |
| A/Shanghai/11/87 | 1:256 |
| A/Guizhou/54/89 | 1:128 |
| A/Beijing/353/89 | 1:512 |
| B/Beijing/1/87 | 1:256 |
| B/Yamagata/16/88 | 1:512 |
| A/PR/8/34 | 1:1024 |
| A/Equi 1/Prague | 1:512 |
| A/Equi 2/Miami | 1:256 |
| A/Equi 2 Fontainebleau | 1:128 |
| A/Swine/Ghent | 1:512 |
| A/Swine/Iowa | 1:1024 |
| A/Swine/Arnsberg | 1:512 |

EXAMPLE 5
Replication of Various Influenza Strains in MDCK 33016 Cells in the Fermenter The cell line MDCK 33016 (DSM ACC2219) was inoculated in Iscove's medium with a cell inoculate of $1 \times 10^5$ cells/ml in a stirred vessel fermenter (working volume 8 l). At an incubation temperature of 37° C., a $pO_2$ of 50±10% (regulated) and a pH of 7.1±0.2 (regulated), the cells proliferated within 4 days to a cell density of $7 \times 10^5$ cells/ml. 8 ml of virus stock solution (either A/PR/8/34 or A/Singapore/6/86 or A/Shanghai/i 1/87 or A/Beijing/1/87 or B/Massachusetts/71 or B/Yamagata/16/88 or B/Panama/45/90) and simultaneously 16 ml of a 1.25% strength trypsin solution were added to these cells and the inoculated cell culture was incubated further at 33° C. The virus replication was determined over 6 days (Table IV).

TABLE IV

Replication of influenza virus strains in the fermenter (cell line MDCK 33016) after infection of a cell culture without change of medium, measured as antigen content (HA units)

| | HA content after days after infection (dpi) | | | | |
|---|---|---|---|---|---|
| | 1 dpi | 3 dpi | 4 dpi | 5 dpi | 6 dpi |
| A/PR/8/34 | 1:64 | 1:512 | 1:1024 | 1:2048 | 1:2048 |
| A/Singapore | 1:32 | 1:512 | 1:2048 | 1:2048 | 1:1024 |
| A/Shanghai | 1:8 | 1:128 | 1:256 | 1:256 | 1:512 |
| A/Beijing | 1:16 | 1:256 | 1:1024 | 1:1024 | n.d. |
| B/Yamagata | 1:8 | 1:128 | 1:512 | 1:512 | n.d. |
| B/Massachusetts | 1:4 | 1:128 | 1:256 | 1:512 | n.d. |
| B/Panama | n.d. | 1:128 | 1:256 | n.d. | 1:1024 |

EXAMPLE 6
Influence of the Infection Dose (m.o.i.) on Virus Replication

The cell line MDCK 13016 (obtained from an MDCK cell culture by selection pressure) was proliferated at 37° C. in ultra CHO medium with a splitting rate of 1:8 to 1:12 twice weekly in a roller bottle which rotated at 16 rpm. Four days after transfer, a cell count of approximately $7.0 \times 10^5$ to $10 \times 10^5$ cells/ml was achieved. The influence of the infective dose (m.o.i.) on the yield of antigen and infectiousness was investigated. Simultaneously to the infection of the now 4 day-old cell culture with the influenza virus strain A/PR/8/34 (m.o.i.=0.5 and m.o.i.=0.005), the cell culture was treated with trypsin (25 μg/ml final concentration) and incubated further at 37° C., and the virus replication was determined over 3 days (Table V).

TABLE V

Replication of influenza virus strain PR/8/34 in the cell line MDCK 13016 in roller bottles after infection with an m.o.i. of 0.5 or 0.005. The assessment of virus replication was carried out by antigen detection (HA) and infectiousness titer ($CCID_{50}$ cell culture infective dose 50% in $log_{10}$)

| | Days after infection | | | | | | | |
|---|---|---|---|---|---|---|---|---|
| | 2 | | 3 | | 4 | | 5 | |
| PR/8/34 | HA | $CCID_{50}$ | HA | $CCID_{50}$ | HA | $CCID_{50}$ | HA | $CCID_{50}$ |
| m.o.i. = 0.5 | 128 | 5.1 | 256 | 5.7 | 512 | 5.3 | 1024 | 5.4 |
| m.o.i. = 0.005 | 64 | 4.9 | 512 | 8.0 | 512 | 8.3 | 1024 | 8.3 |

The determination of the $CCID_{50}$ can in this case be carried out, for example, according to the method which is described in Paul, Zell-und Gewebekultur [Cell and tissue culture](1980), p. 395.

EXAMPLE 7

Influence of Media Substitution on Virus Replication

The cell line MDCK 33016 (DSM ACC2219) was proliferated at 37° C. in Iscove's medium with a splitting rate of 1:8 to 1:12 twice weekly in a roller bottle which rotated at 16 rpm. Four days after transfer, a cell count of approximately $7.0 \times 10^5$ to $10 \times 10^5$ cells/ml was achieved. The influence of a media substitution on the yield of antigen and infectiousness was investigated. The now 4-day old cell culture was infected with the influenza virus strain A/PR/8/34 (m.o.i.=0.05), the trypsin addition (20 μg/ml final concentration in the roller bottle) being carried out by mixing the virus inoculum with the trypsin stock solution. The cell culture was treated with additions of media and incubated further at 33° C., and the virus replication was determined over 5 days (Table VI).

TABLE VI

Replication of influenza A/PR/8/34 in roller bottles (cell line MDCK 33016); addition of 5% (final concentration) of a triple-concentrated Iscove's medium, of glucose (final concentration 3%) or glucose and casein hydrolysate (final concentration 3% or 0.1%) measured as antigen content (HA units)

| | HA content after days after infection (dpi) | | | |
|---|---|---|---|---|
| Addition | 1 dpi | 3 dpi | 4 dpi | 5 dpi |
| —<br>(control) | 1:16 | 1:256 | 1:1024 | 1:1024 |
| 3x Iscove's | 1:8 | 1:128 | 1:1024 | 1:2048 |
| Glucose | 1:32 | 1:512 | 1:2048 | 1:2048 |
| Glucose/casein hydrolysate | 1:8 | 1:128 | 1:512 | 1:1024 |

EXAMPLE 8

Replication of Influenza Viruses in MDCK 33016 Cells in the Fermenter and Obtainment of the Viruses The cell line MDCK 33016 (ACC2219) was inoculated in Iscove's medium with a cell inoculate of $0.5 \times 10^5$ cells/ml in a stirred vessel fermenter (working volume 10 l). At an incubation temperature of 37° C., a $pO_2$ of 55±10% (regulated) and a pH of 7.1±0.2 (regulated), the cells proliferated within 4 days to a cell density of $7 \times 10^5$ cells/ml. 0.1 ml of virus stock solution (A/Singapore/6/86; m.o.i. about 0.0015) and simultaneously 16 ml of a 1.25% strength trypsin solution were added to these cells and the inoculated cell culture was incubated further at 33° C. The virus replication was determined after 5 days and the virus was harvested. Cells and cell residues were removed by tangential flow filtration (Sarcoton Mini-Microsart Module with 0.45 μm pore size; filtration procedure according to the instructions of the manufacturer), no loss of antigen (measured as HA) being detectable in the filtrate. The virus material was concentrated from 9.51 to 600 ml by fresh tangential flow filtration (Sartocon Mini-Ultrasart Module with 100,000 NMWS (nominal molecular weight separation limit); filtration procedure according to the instructions of the manufacturer). The amount of antigen in the concentrate was 5120 HA units (start 256 HA units; concentration factor 20), while the infectiousness in the concentrate was 9.2 $log_{10}$ $CCID_{50}$ (start 8.9 $log_{10}$ $CCID_{50}$; concentration factor 16); the loss of antigen and infectiousness was less than 1%, measured in the filtrate after the 100,000 NMWS filtration.

EXAMPLE 9

Replication of the Influenza Viruses in MDCK 33016 Cells in the Perfusion Fermenter $1.6 \times 10^8$ cells of the cell line MDCK 33016 (DSM ACC2219) were suspended in UltraCHO medium ($0.8 \times 10^5$ cells/ml) in the reactor vessel of Biostat MD (Braun Biotech Int., Melsungen, Germany) with an effective volume of 2000 ml and proliferated at 37° C. in perfusion operation with a rising flow rate (entry of oxygen by hose aeration (oxygen regulation 40±10% $pO_2$); pH regulation pH ±7.2; cell retention by spin filter >95%). The live cell count increased within 11 days by 200-fold to $175 \times 10^5$ cells/ml (Table VIIIa). 1990 ml of this cell culture were transferred to a 2nd perfusion fermenter (working volume 5 l), while the remaining cells were made up to 2000 ml again with medium and cell proliferation was carried out again in perfusion operation. In the 2nd perfusion fermenter (virus infection), the cells were infected with the influenza virus strain A/PR/8/34 (m.o.i.=0.01) with simultaneous addition of trypsin (10 μg/ml final concentration) and incubated for 1 h. The fermenter was then incubated further in perfusion operation (regulation of $pO_2$:40±10% and pH:£7.2). On the first day after infection, incubation was carried out at 37° C. and the virus harvest in the perfused cell culture supernatant was discarded. From the 2nd day after infection, virus replication was carried out at 33° C. and the perfusion rate of 2 fermenter volumes/day was reduced to 0 within 7 days. The trypsin necessary for virus replication was present in the UltraCHO medium which was used for the perfusion in a concentration of 10 μg/ml. The virus harvest (=perfused cell culture supernatant) was collected at 4° C. and the virus replication over 7 days was determined as the amount of antigen (Table VIIIb).

TABLE VIIIa

Replication of MDCK 33016 cells in the perfusion fermenter

| Day | Live cell count [$10^5$/ml] | Total cell count [$10^5$/ml] | Perfusion [1/day] |
|---|---|---|---|
| 0 | 0.6 | 0.6 | 0 |
| 3 | 8.0 | 8.3 | 0 |
| 4 | 14.6 | 17.5 | 1.1 |
| 5 | 33.3 | 34.7 | 1.1 |
| 6 | 49.8 | 53.6 | 2.1 |
| 7 | 84.5 | 85.6 | 3.9 |
| 9 | 82.6 | 84.9 | 4.0 |
| 9 | 100.8 | 104.8 | 4.1 |
| 10 | 148.5 | 151.0 | 4.0 |
| 11 | 175.8 | 179.6 | 3.9 |

TABLE VIIIb

Replication of influenza A/PR/8/34 in the perfusion fermenter (cell line MDCK 33016), measured as antigen content (HA units) in the cumulated perfused cell culture supernatant

| Day after infection | HA content in virus harvest | Medium addition (perfusion) | Total amount virus harvest |
|---|---|---|---|
| 1 | <4 | 4.1 | 0.1 |
| 2 | 8 | 4.1 | 4.1 |
| 3 | 64 | 3.1 | 7.1 |
| 4 | 256 | 2.1 | 9.1 |
| 5 | 2048 | 2.1 | 11.1 |
| 6 | 4096 | 2.1 | 12.1 |
| 7 | 4096 | 0.1 | 12.1 |

EXAMPLE 10

Preparation of an Experimental Influenza Vaccine

An experimental vaccine was prepared from influenza virus A/PR/8/34 from Example 2—A/PR/8 replicated at 37° C.—(Experiment 2; vaccine A) and Example 4—A/PR/8 replicated at 33° C.—(vaccine B). The influenza viruses in the cell culture medium were separated from cells and cell fragments by low-speed centrifugation (2000 g, 20 min, 4° C.) and purified by a sucrose gradient centrifugation (10 to 50% (wt/wt) of linear sucrose gradient, 30,000 g, 2 h, 4° C.). The influenza virus-containing band was obtained, diluted 1:10 with PBS pH 7.2, and sedimented at 20,000 rpm, and the pellet was taken up in PBS (volume 50% of the original cell culture medium). The influenza viruses were inactivated with formaldehyde (addition twice of 0.025% of a 35% strength formaldehyde solution at an interval of 24 h, incubation at 20° C. with stirring). 10 NMRI mice each, 18 to 20 g in weight, were inoculated with 0.3 ml each of these inactivated experimental vaccines on day 0 and day 28 by subcutaneous injection. 2 and 4 weeks after the inoculation and also 1 and 2 weeks after revaccination, blood was taken from the animals to determine the titer of neutralizing antibodies against A/PR/8/34. To determine the protection rate, the mice were exposed 2 weeks after revaccination (6 weeks after the start of the experiment) by intranasal administration of 1000 $LD_{50}$ (lethal dose 50%). The results of the experiment are compiled in Table IX.

TABLE IX

Efficacy of experimental vaccines: for vaccine A the influenza virus A/PR/8/34 was replicated at 37° C. and for vaccine B at 33° C. The titer of neutralizing antibodies against A/PR/8 and also the protection rate after exposure of the mice were investigated

| | Titer of neutralizing antibodies/ml* | | | | Protection rate Number |
|---|---|---|---|---|---|
| | 2 w pvacc | 4 w pvacc | 1 w prevacc | 2 w prevacc | living/total |
| Vaccine A | <28 | 56 | 676 | 1,620 | 1/10 |
| Vaccine B | 112 | 1,549 | 44,670 | 112,200 | 9/10 |

*Weeks after vaccination (w pvacc) and weeks after revaccination (w prevacc)

The experiments confirm that influenza viruses which had been replicated at 37° C. in cell culture with a high antigen yield (HA titer) only induced a low neutralizing antibody titer in the mouse and barely provided protection, while influenza viruses which had been replicated at 33° C. in cell culture also with a high antigen yield (titer) induced very high neutralizing antibody titers in the mouse and led to very good protection.

What is claimed:

1. An MDCK cell which can be infected by influenza viruses, wherein the MDCK cell is adapted to growth in suspension, and wherein the MDCK cell is adapted to growth in serum-free medium.

2. A process for the replication of influenza viruses in cell culture, which comprises:
    (i) proliferating MDCK cells wherein said cells can be infected by influenza viruses, wherein said cells are adapted to growth in suspension, and wherein said cells are adapted for growth in serum-free medium;
    (ii) infecting the cells with influenza viruses;
    (iii) shortly before infection, simultaneously to infection, or shortly after infection, adding to the cell suspension a protease to cleave the precursor protein of hemagglutinin; and
    (iv) isolating the influenza viruses replicated in the cells.

3. The process as claimed in claim 2, the culture of the cells taking place in the perfusion system.

4. The process as claimed in claim 2, the culture of the cells taking place in the batch process.

5. The process as claimed in claim 2, the pH of the culture medium in step (i) being in the range from 6.6 to 7.8.

6. The process as claimed in claim 5, the pH of the culture medium being in the range from 6.8 to 7.3.

7. The process as claimed in claim 2, the infection with influenza viruses being carried out when the cell culture has achieved a cell density of about 8 to $25 \times 10^5$ cells/ml (batch process) or of about 5 to $20 \times 10^6$ cells/ml (perfusion process).

8. The process a claimed in claim 2, the infection of the cells with influenza viruses being carried out at an m.o.i. (multiplicity of infection) of about 0.001 to 10.

9. The process as claimed in claim 8, the infection being carried out at an m.o.i. of about 0.002 to 0.5.

10. The process as claimed in claim 2, the protease being a serine protease.

11. The process as claimed in claim 10, the serine protease being trypsin.

12. The process as claimed in claim 11, trypsin being added up to a final concentration in the culture medium of 1 to 200 μg/ml.

13. The process as claimed in claim 12, the final concentration of trypsin in the culture medium being in the range from 5 to 50 μg/ml.

14. The process as claimed in claim 2, the infected cells being cultured for 2 to 10 days.

15. The process as claimed in claim 14, the infected cells being cultured for 3 to 7 days.

16. The process as claimed in claim 2, the infected cells being cultured at 30° C. to 36° C.

17. The process as claimed in claim 16, the infected cells being cultured at 32° C. to 34° C.

18. The process as claimed in claim 2, the harvesting and isolation of the replicated viruses being carried out 2 to 10 days after infection.

19. The process as claimed in claim 18, the harvesting and isolation of the viruses being carried out 3 to 7 days after infection.

20. The method of claim 2 wherein said protease is added to the cell suspension before infection.

21. The method of claim 2 wherein said protease is added to the cell suspension simultaneous to infection.

22. The method of claim 2 wherein said protease is added to the cell suspension after infection.

23. A process for the replication of influenza viruses in cell culture, which comprises:

(i) proliferating MDCK cells wherein said cells can be infected by influenza viruses and wherein said cells are adapted for growth in suspension;

(ii) infecting the cells with influenza viruses;

(iii) shortly before infection, simultaneously to infection, or shortly after infection adding to the cell suspension a protease to cleave the precursor protein of hemagglutinin; and (iv) isolating the influenza viruses replicated in the cells.

24. The process as claimed in claim 23, the culture of the cells taking place in the perfusion system.

25. The process as claimed in claim 23, the culture of the cells taking place in the batch process.

26. The process as claimed in claim 23, the pH of the culture medium in step (i) being in the range from 6.6 to 7.8.

27. The process as claimed in claim 26, the pH of the culture medium being in the range from 6.8 to 7.3.

28. The process as claimed in claim 23, the infection with influenza viruses being carried out when the cell culture has achieved a cell density of about 8 to $25 \times 10^5$ cells/ml (batch process) or of about 5 to $20 \times 10^6$ cells/ml (perfusion process).

29. The process as claimed in claim 23, the infection of the cells with influenza viruses being carried out at an m.o.i. (multiplicity of infection) of about 0.001 to 10.

30. The process as claimed in claim 29, the infection being carried out at an m.o.i. of about 0.002 to 0.5.

31. The process as claimed in claim 23, the protease being a serine protease.

32. The process as claimed in claim 31, the serine protease being trypsin.

33. The process as claimed in claim 32, trypsin being added up to a final concentration in the culture medium of 1 to 200 μg/ml.

34. The process as claimed in claim 33, the final concentration of trypsin in the culture medium being in the range from 5 to 50 μg/ml.

35. The process as claimed in claim 23, the infected cells being cultured for 2 to 10 days.

36. The process as claimed in claim 35, the infected cells being cultured for 3 to 7 days.

37. The process as claimed in claim 23, the infected cells being cultured at 30° C. to 36° C.

38. The process as claimed in claim 37, the infected cells being cultured at 32° C. to 34° C.

39. The process as claimed in claim 23, the harvesting and isolation of the replicated viruses being carried out 2 to 10 days after infection.

40. The process as claimed in claim 39, the harvesting and isolation of the viruses being carried out 3 to 7 days after infection.

41. the process of claim 23 wherein the protease is added to the cell suspension before infection.

42. The process of claim 23 wherein said protease is added to the cell suspension simultaneous to infection.

43. The process of claim 23 wherein said protease is added to the cell suspension after infection.

* * * * *